(12) United States Patent
Yan et al.

(10) Patent No.: US 9,551,699 B2
(45) Date of Patent: Jan. 24, 2017

(54) TESTING OF BLOOD COAGULATION CHARACTERISTICS

(71) Applicant: Micropoint Bioscience, Inc., Santa Clara, CA (US)

(72) Inventors: Pingyi Yan, Guangdong (CN); Haitao Huang, San Jose, CA (US); Shenyu Wang, Guangdong (CN); Huihui Lu, Guangdong (CN)

(73) Assignee: Micropoint Bioscience, Inc., Santa Clara, CA (US)

( * ) Notice: Subject to any disclaimer, the term of this patent is extended or adjusted under 35 U.S.C. 154(b) by 1053 days.

(21) Appl. No.: 13/632,843

(22) Filed: Oct. 1, 2012

(65) Prior Publication Data

US 2014/0014509 A1    Jan. 16, 2014

Related U.S. Application Data

(60) Provisional application No. 61/671,810, filed on Jul. 16, 2012.

(51) Int. Cl.
*G01N 33/487* (2006.01)
*G01N 33/49* (2006.01)
*G01N 33/86* (2006.01)
*C12Q 1/56* (2006.01)
*A61B 5/00* (2006.01)
*A61B 5/05* (2006.01)

(52) U.S. Cl.
CPC ............ *G01N 33/4905* (2013.01); *C12Q 1/56* (2013.01); *G01N 33/86* (2013.01)

(58) Field of Classification Search
CPC ...... C12Q 1/56; G01N 33/4905; G01N 33/86; G01N 27/28; G01N 27/416; G01N 33/50; G01N 33/49; G01N 27/26; G01N 27/00
See application file for complete search history.

(56) References Cited

U.S. PATENT DOCUMENTS 6,046,051 A * 4/2000 Jina ..................... G01N 33/86
                                                     422/403
6,620,310 B1   9/2003 Ohara et al.
(Continued)

FOREIGN PATENT DOCUMENTS

EP       0932041        7/1999
WO    WO2014014484    1/2014
WO    WO2014014485    1/2014

OTHER PUBLICATIONS

PCT Search Report mailed Feb. 15, 2013 for PCT application No. PCT/US12/59224, 12 pages.
(Continued)

*Primary Examiner* — Michael Kahelin
*Assistant Examiner* — Mitchell E Alter
(74) *Attorney, Agent, or Firm* — Lee & Hayes, PLLC; Benjamin A. Keim

(57) ABSTRACT

In some examples, a device applies an electrical potential difference across a blood sample. The device measures an electrical signal that passes through the blood sample over a duration of time to obtain a plurality of measurements representing a measurement function of time. An accumulative property of the measurement function may be determined such that the accumulative property correlates to a blood coagulation characteristic.

16 Claims, 15 Drawing Sheets

(56) References Cited

U.S. PATENT DOCUMENTS

| 7,021,122 B1* | 4/2006 | Rosemberg | G01N 11/04 |
| | | | 73/304 C |
| 2011/0109325 A1 | 5/2011 | Huang et al. | |
| 2014/0014533 A1 | 1/2014 | Yan et al. | |

OTHER PUBLICATIONS

PCT Search Report mailed Feb. 20, 2013 for PCT application No. PCT/US12/59221, 12 pages.
Office Action for U.S. Appl. No. 13/632,393, mailed on Jan. 22, 2014, Pingyi Yan, "Determining Blood Coagulation Characteristics", 18 pages.
International Preliminary Report on Patentability dated Jan. 20, 2015 in PCT Application No. PCT/US2012/059224.
International Preliminary Report on Patentability dated Jan. 20, 2015 in PCT Application No. PCT/US2012/059221.
Office Action mailed Aug. 12, 2015 in U.S. Appl. No. 13/632,393.
Office Action mailed Dec. 2, 2014 in U.S. Appl. No. 13/632,393.

* cited by examiner

TESTING OF BLOOD COAGULATION CHARACTERISTICS

CROSS-REFERENCE TO RELATED APPLICATION

This application claims the benefit of, and priority to, U.S. Provisional Patent Application No. 61/671,810, filed Jul. 16, 2012, which is incorporated by reference herein in its entirety.

BACKGROUND

Medical devices and medical testing may be used to diagnose, identify, monitor or otherwise determine health related information. As one example, blood coagulation screening tests, such as Prothrombin Time (PT), Activated Partial Thromboplastin Time (APTT), Activated Clotting Time (ACT), fibrinogen content (FIB) and Thrombin Time (TT) may be performed by clinical laboratories, health practitioners, and the like. Each of these tests relates to a type of blood coagulation characteristic under a certain condition.

Clinicians may use these tests for various purposes, such as to monitor anticoagulant therapy, to screen for a single factor deficiency, to screen for multiple factor deficiencies and/or to screen for specific or non-specific inhibitors. As one example, unfractionated heparin therapy is widely used as a treatment for thromboembolic (obstructive blood clots) disorders. In some cases, heparin therapy, or the amount of heparin administered, is determined based on the result of the APTT or ACT tests. However, there are many pre-analytical and analytical variables that can affect the PT, APTT, ACT, FIB or TT measurements, often giving dramatically different measurements from one test device or laboratory to another. This can produce a variance in the amount of a drug (e.g., heparin) or other therapy administered to the patient, and may lead to less than optimal therapeutic results.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
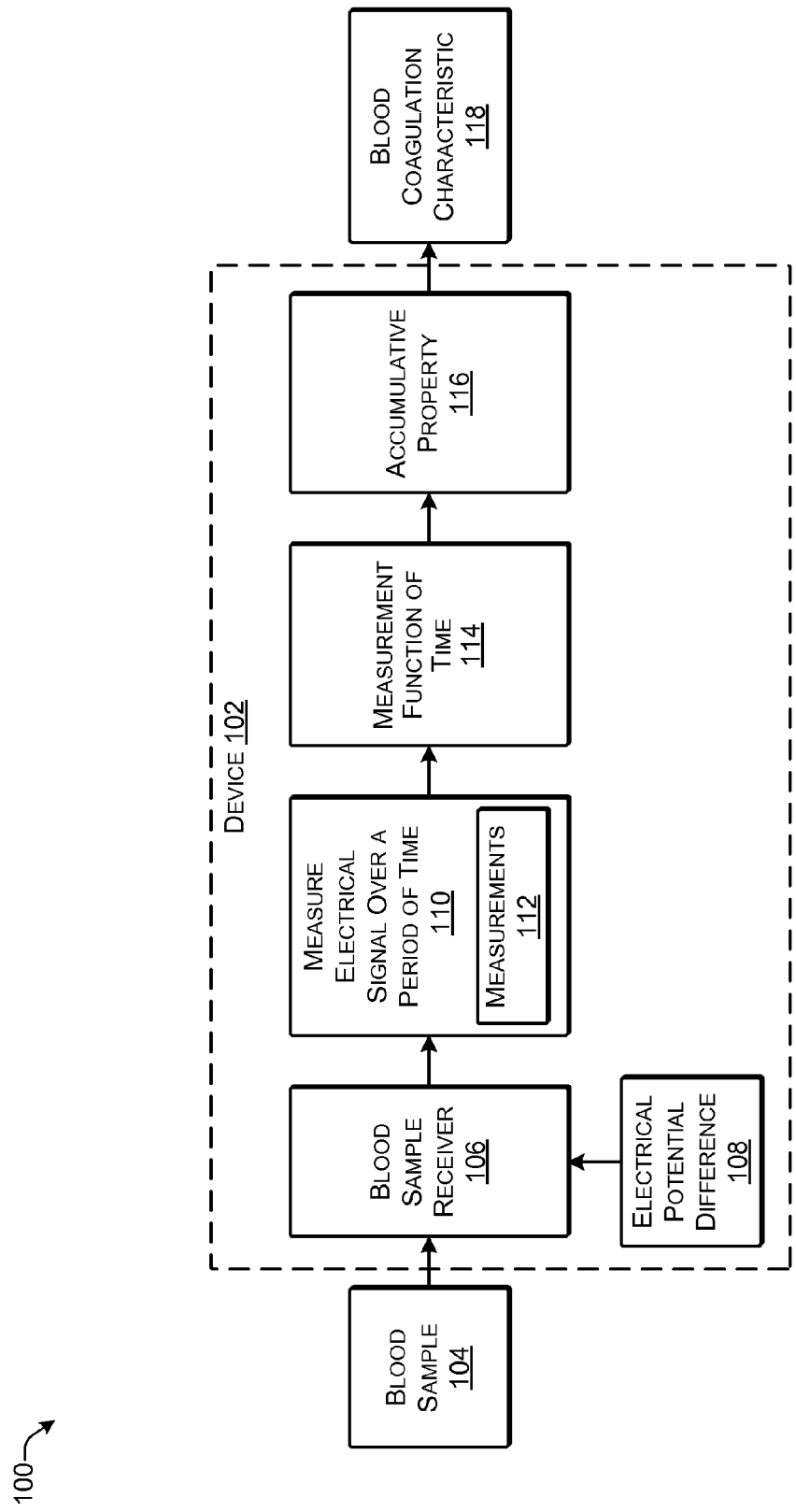
FIG. 1 illustrates an example framework for determining blood coagulation information according to some implementations.

This disclosure includes techniques and arrangements for determining blood sample properties that are indicative of a blood coagulation characteristic of the blood sample. In some examples, a blood sample is introduced into a sample receiver comprising a plurality of electrodes so that at least part of the blood sample and the plurality of electrodes are connected in an electrical circuit. For instance, the sample receiver and the electrical circuit may be implemented in a device. The device may apply an electrical potential difference over the plurality of electrodes and at least part of the blood sample. The device can measure an electrical signal passing through the blood sample, such as by taking a measurement at an output terminal of the circuit. The measurements may be taken over a measurement time duration to obtain a plurality of measurements representing a measurement function of time. An accumulative property of the measurement function can be determined, such that the accumulative property correlates to a blood coagulation characteristic. The blood coagulation characteristic can be determined based at least in part on the accumulative property applied to the measurement function. In some cases, the accumulative property may be based at least in part on an area associated with a segment of a curve of the electrical signal plotted over time. In other cases, the accumulative property may be based at least in part on a change in amplitude of a portion of a curve of the electrical signal plotted over time.

Some examples herein may consider at least a portion of a curve of the measurements taken over time, and can calculate quantities representative of blood coagulation characteristics based on the measurement curve. In contrast, a conventional technique for testing blood coagulation includes detecting an endpoint or end state of a blood sample (e.g., detecting a color change, a flat point of an impedance curve, a viscosity, or other physical property). Thus, conventional techniques may merely focus on determining a particular end state of the sample.

Some implementations herein are based at least partially on a premise that during coagulation there is an internal friction that gradually builds up against electrical conductivity, thus resulting in an accumulated conductive energy loss. Accordingly, this accumulative property is used in some examples herein to characterize the coagulation property of a blood sample. The accumulative property, as disclosed herein, may be an accumulated property of the acquired measurement function, and may be related to at least two data points (measurements) in the measurement function over a period of time, as opposed to a property at a single point of a curve (such as viscosity or impedance of an end-state of coagulation).

In addition, some implementations herein are based at least in part on the intuition that the accumulated properties of the measurement function tells a more accurate and complete story of the coagulation process than the single end-state property measurements conventionally used. Theories and explanations may be hypothesized herein to rationalize the observations. However, the usefulness of the disclosed methods and devices based thereon, and more importantly the scope of the claims provided in this application, do not rely on, nor are limited by, the correctness or soundness of any hypothesized theories, premises or explanations. Further, the disclosure does not require a superior performance of the disclosed methods, devices or techniques.

For discussion purposes, some example implementations are described in the environment of a test device and system for testing blood coagulation properties. However, the implementations herein are not limited to the particular examples provided, and may be extended to other types of devices, apparatuses and systems, and other types of testing, as will be apparent to those of skill in the art in light of the disclosure herein.

Example Framework

FIG. 1 illustrates an example framework 100 for testing for blood coagulation characteristics according to some implementations. In some examples, rather than detecting an end state of a blood sample, an analytical technique is applied to determine an accumulative property of a plurality of measurements taken over time during the process of coagulation. At least a portion of the framework 100 may be performed on a device 102. In other examples, multiple devices may carry out the framework 100, such as performing a measuring function on a first device and performing a calculating function on a second device that receives measurement information from the first device. Depending at least in part on the type of the device 102, a user of the device 102 may be any of a medical or clinical professional, a patient, a family member of a patient, a caregiver of a patient, or any other person using the device 102.

In the framework 100, a blood sample 104 may be received by a blood sample receiver 106. As several examples, a small blood sample 104 may be applied to a reagent strip, a cartridge, a cassette, a sample receptor, or the like, that may be part of the device 102, or that may be introduced to the device 102, inserted into the device 102, connected to the device 102, etc. Accordingly, implementations herein are not limited to any particular apparatus or technique for providing a blood sample 104 to a blood sample receiver 106 of the device 102.

An electrical potential difference 108 may be applied to the blood sample 104 received by the blood sample receiver 106. As indicated at 110, an electrical signal passing through the blood sample may be measured over a period of time to produce a plurality of measurements 112. For example, the measurements 112 may indicate at least one of a change in voltage or a change in current over a period of time as a result of applying the electrical potential difference 108 to the blood sample 104. As another example, the measurements 112 may be derivative values of an electrical signal measured over time.

Based on the measurements 112 and the period of time, a measurement function of time 114 may be determined. In some examples, the measurement function of time 114 may be expressed as a graphic representation such as a curve that represents the measured electrical signal over the period of time. However, in other examples, a graphic representation need not be produced in order to apply or use the measurement function of time 114. Based on the measurement function of time 114, at least one accumulative property 116 may be determined. For example, the accumulative property 116 may correspond to a portion of the measurement function of time, and may be correlated to a blood coagulation characteristic 118. In some examples, the curve of the measurement function (e.g., the signal curve) may be divided into four processes, each of which may be correlated to a different blood coagulation condition. Information related to the blood coagulation characteristic 118 may be provided to any of various targets, such as a display, a storage medium, and/or a computing device.

Example Sample Receptor

Figure 2:
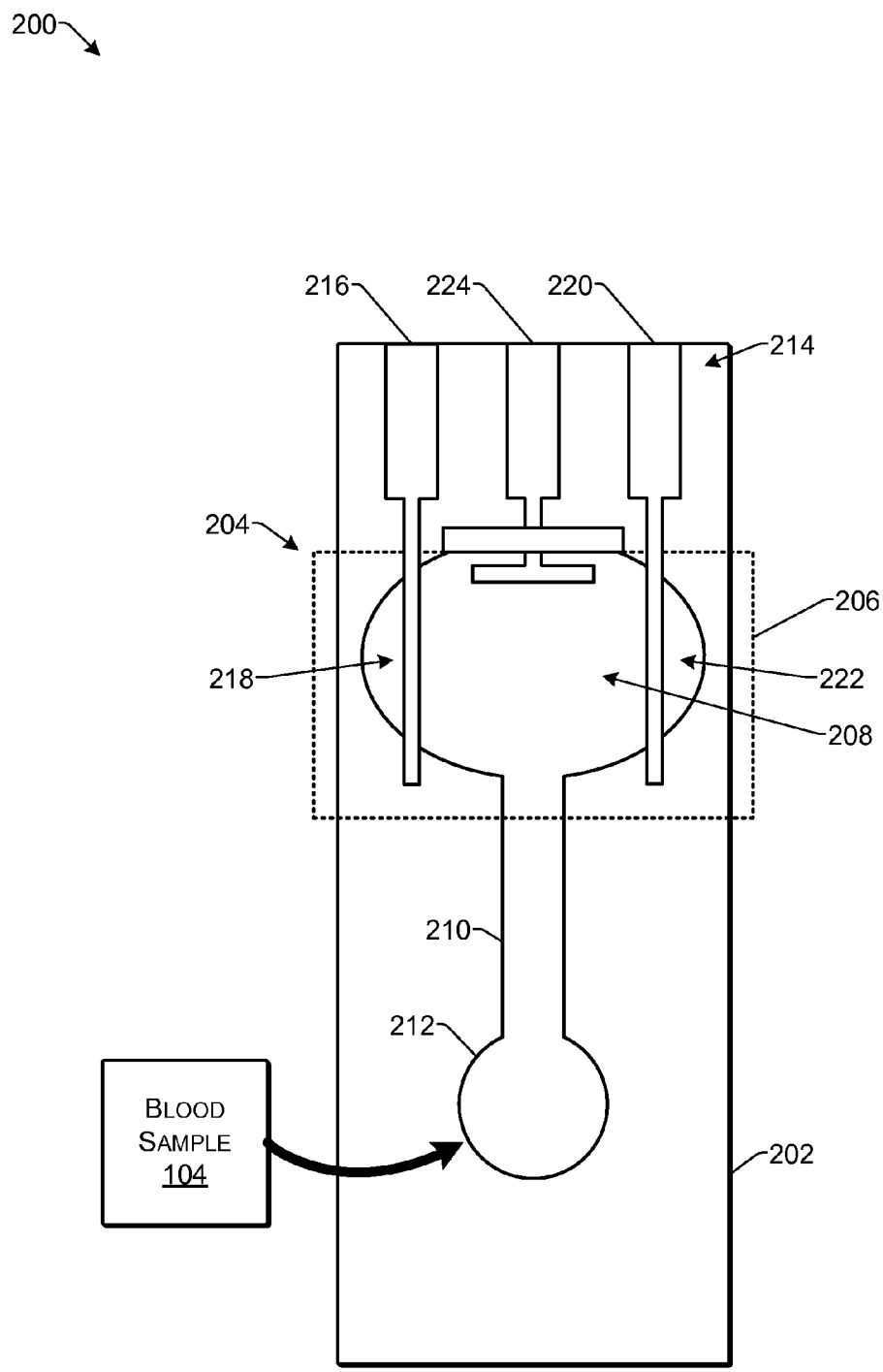
FIG. 2 illustrates an example sample receptor according to some implementations.

FIG. 2 illustrates an example sample receptor 200 according to some implementations. In this example, the sample receptor 200 is illustrated as a test strip or test cartridge 202. A reaction area 204, as indicated by the dashed line 206 may include one or more reagents 208 or other substance selected for one or more types of tests. Usually, different tests (e.g., PT, APTT, ACT, FIB or TT) have their own reagent 208 or other substance that is suitable for detecting the particular characteristic. As one example, the reagent 208 may be pre-applied (e.g., printed, deposited, etc.) and fixed at the reaction area 204.

The test cartridge 202 further includes a delivery channel 210 that may connect the reaction area 204 with a sample well or receptacle 212. For example, a quantity of sample blood may be delivered to the receptacle 212 as the blood sample 104. The sample blood may flow through the delivery channel 210 to the reaction area 204. For example, capillary action may draw the blood sample 104 from the sample receptacle 212 to the reaction area 204.

The test cartridge 202 may further include a plurality of electrodes 214 to form an electrochemical cell. For example, a first electrode 216 may connect to a first portion 218 of the reaction area 204 and a second electrode 220 may connect to a second portion 222 of the reaction area 204. A third electrode 224 also connects to the reaction area 204. In this example, the electrochemical cell at the reaction area 204 consists of three electrodes, such as a working electrode, a counter electrode and a reference electrode. In other examples, the counter and reference electrodes may be combined to provide a two-electrode configuration.

Accordingly, it may be seen that when the blood from the blood sample enters the reaction area 204, the blood sample 104 is positioned between a plurality of electrodes, such as the first electrode 216 and the second electrode 220. Further, the blood sample 104 may interact with the reagent 208 or other substance in the reaction area 204 in examples in which a reagent or other substance is used during testing of a blood sample. Additionally, while a single electrochemical cell is shown in this example, in other examples, multiple electrochemical cells may be included to provide multiple reaction areas 204. For instance, different reaction areas 204 may include different types of reagents 208 or substances suitable for different types of tests. These reaction areas could be connected through channels to a single sample receptacle 212.

One application for which the test cartridge 202 may be applied is a heparin test. For example, a heparin neutralizer may be a reagent 208 located in the reaction area 204 adjacent to the electrodes. A blood sample 104 is introduced at the sample receptacle 212 and is delivered by the delivery channels 210 to the reaction area 204. Within the reaction area 204, the blood sample reacts with the reagent 208, which may trigger a series of biochemical reactions leading to coagulation. In the reaction area 204, the blood sample 104 is in contact with the plurality of electrodes 214. As discussed additionally below, when the test cartridge 202 is inserted into a device, the electrodes 214 and the blood sample 104 located in the reaction area 204 become an electrochemical part of a complete circuit for testing of the blood sample 104. For instance, the device may apply an electrical potential difference over the electrodes 214 to detect an electrical signal at an output terminal of the circuit over a period of time (i.e., a measurement time duration) to obtain a plurality of measurements which represent a function of time (i.e., a measurement function of time).

Example System

Figure 3:
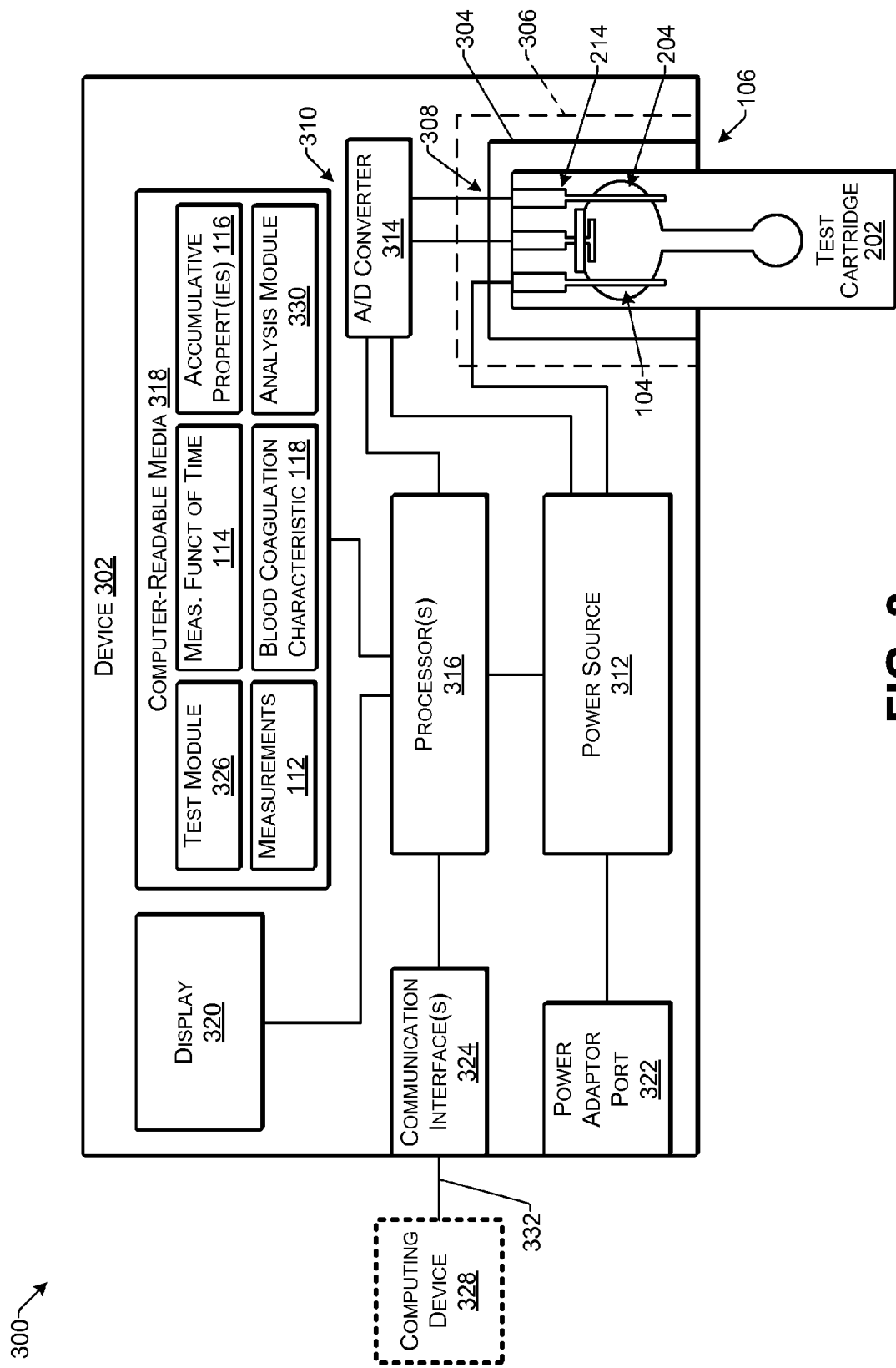
FIG. 3 illustrates select components of an example system including a device for testing a blood coagulation characteristic according to some implementations.

FIG. 3 illustrates an example architecture of a system 300 to take measurements that may be used for determining blood coagulation properties according to some implementations. The system 300 includes a device 302, which may be a testing device, or other device able to at least apply an electrical potential difference to a blood sample 104, as discussed above. In some examples, the device 302 may correspond to the device 102 discussed above and/or may execute at least a portion of the framework 100 discussed above with respect to FIG. 1.

The device 302 includes the blood sample receiver 106, which in this example includes a cartridge receiver 304 and a heater 306. For example, the heater 306 may ensure that the blood sample 104 is maintained at a uniform temperature during testing to ensure uniformity of testing across a plurality of samples. Additionally, in other examples, the blood sample receiver 106 may have a different configuration, depending on the technique actually used for delivering a blood sample to the device 302.

The device 302 may further include a plurality of electrical connections 308 for connecting the electrodes 214 of the test cartridge 202 with a circuit 310 of the device 302. For example, the electrodes 214 may be connected to a power source 312 and an analog/digital converter 314. The power source 312 may provide an electrical potential difference across the blood sample 104 in the reaction area 214 of the test cartridge 202 during testing of the blood sample 104. The A/D converter 314 may measure a resulting electrical signal, such as at an output terminal. In some cases, the output terminal may correspond to one or more of the electrodes 214.

The device 302 may further include one or more processors 316, one or more computer-readable media 318, a display 320, a power adapter port 322, and one or more communication interfaces 324, such as an external data port or other suitable communication interface, as discussed below. For example, the processor(s) 316 may be any of a control logic circuit, a central processing unit, a microprocessor, or other suitable type of processor. In some examples, each processor 316 may itself comprise one or more processors or processing cores. Alternatively, in other examples, the device 302 may be a thin component having minimal processing resources merely sufficient to execute a test function or test module 326 during use of the device 302, while additional processing may be executed remotely on a computing device 328 or other device able to communicate with the device 302 through the communication interface 324.

Depending on the configuration of the device 302, the computer-readable media 318 may be an example of tangible non-transitory computer storage media and may include volatile and nonvolatile memory and/or removable and non-removable media implemented in any type of technology for storage of information such as computer-readable instructions, data structures, program modules or other data. Such computer-readable media 318 may include, but is not limited to, RAM, ROM, EEPROM, flash memory or other computer-readable media technology, computer storage technology, or any other medium that can be used to store information and which can be accessed by the processor 316 directly or through another computing device. Accordingly, the computer-readable media 318 may include computer storage media able to store and maintain instructions, modules or components executable by the processor 316.

The computer-readable media 318 may be used to store any number of functional components that are executable by the processor 316. In some implementations, these functional components comprise instructions, code or programs that are executable by the processor 316 and that, when executed, implement operational logic for performing the actions attributed to the device 302. Functional components of the device 302 maintained in the computer-readable media 318 may include the test module 326, executable by the processor 316, to perform testing on a blood sample, such as for applying an electrical potential difference across the blood sample and obtaining measurements of an electrical signal. The functional components may further include an analysis module 330, which may be executed by the processor 316 to perform some functions described herein, such as determining a measurement function of time 114, one or more corresponding accumulative properties 116 and/or a blood coagulation characteristic 118. For example, the analysis module 330 may further determine a blood coagulation characteristic based at least in part on an accumulative property 116 and/or the measurements 112 or measurement function of time 114. Additionally, the computer readable media 318 may store data such as measurements 112, the measurement function of time 114, the accumulative propert(ies) 116, the blood coagulation characteristics 118 or information related thereto, and so forth. In addition, depending on the type of the device 302, the computer-readable media 318 may also optionally include other functional components and data, such as a user interface module, a communication module, medical histories, past blood coagulation test results or other modules, applications, programs, drivers, data, and the like.

The measurements 112 taken by the device 302 with respect to the blood sample 104 may be stored in the computer-readable media 318 and analyzed, such as by execution of the analysis module 330 by the processor 316. The analysis module 330 may determine a quantitative value of an accumulative property 116 of the measurement function 114. The accumulative property 116 may be derived or selected empirically prior to taking the measurements 112, or in some cases, prior to making the device 302. For example, the standard for selecting a suitable accumulative property 116 is usually to obtain a good correlation with a blood coagulation characteristic 118 to enable the accumulative property 116 to be used to determine the blood coagulation characteristic 118.

In some examples, the processing for determining the measurement function of time 114, the accumulative property 116 and/or the blood coagulation characteristics 118 may be performed by the processor 316 executing the analysis module 330 on the device 302. In other examples, some or all of the processing may be performed by the external computing device 328. For example, the device 302 may provide the measurements 112 to the computing device 328, and the computing device 328 may execute an analysis module 330 on a processor of the computing device 328 to determine the measurement function of time 114, apply the accumulative property 116 and/or determine the blood coagulation characteristic 118. In such a situation, the test module 326, or other suitable application or communication module on the device 302, may communicate with the computing device 328 over a connection 332 to provide the measurements 112 to the computing device 328. In other examples, the computing device 328 may expose programmatic interfaces or APIs (application programming interfaces) that the device 302 can use to provide the measurements 112. In other examples, rather than providing the measurements 112, the device 302 may provide the blood coagulation characteristic 118 or information related to the blood coagulation characteristic to the computing device 328.

The test device 102 may include one or more communication interfaces 324 that may be used to communicate with the computing device 328 for accessing and interacting with one or more modules on the computing device 328. In some examples, the communication interface 324 may support wired and/or wireless connection 332 to various networks, such as cellular networks, radio communications, Wi-Fi networks, short-range or near-field networks (e.g., Bluetooth®), infrared signals, local area networks, wide area networks, the Internet, a direct cable connection, and so forth. As one example, the communication interface 324 may include a USB (universal serial bus) port, an IEEE 802.3 port, or other wired connection. In other examples, the communication interface 324 may allow the device 302 to access a wireless communication network or device.

FIG. 3 further illustrates the display 320, which may be passive, emissive or any other form of display. In some examples, the display 320 may include any suitable type, such as a liquid crystal display, plasma display, light emitting diode display, organic light emitting diode display, and so forth. Additionally, in some examples, the display 320 may have a touch sensor associated therewith to enable touch inputs from a user. Further, in other examples, the test device 302 may not include a display.

The test device 302 may further be equipped with various other input/output (I/O) components (not shown in FIG. 3). Such I/O components may include various user controls (e.g., buttons, a joystick, a keypad, etc.), speakers, a microphone and so forth. For example, the device 302 may include suitable drivers configured to accept input from a keypad or other user controls and devices included as the I/O components. Additionally, depending on the type, the device 302 may include various other components that are not shown in this example.

Example Measurement Function

Blood clotting may include three stages. During a first stage, vessel wall injury or trauma triggers the attachment and activation of platelets. In the second stage, activated platelets provide surfaces for the assembly and activation of coagulation factors and complexes. In the third stage, the coagulation factors interact to produce thrombin, which converts fibrinogen to fibrin. Fibrin strands bind aggregated platelets to help secure a platelet-fibrin hemostatic plug. The second and third stages of blood coagulation may be referred to as a coagulation cascade for the interaction among each of the coagulation factors. These are the major stages of blood clotting, because of the formation of thrombin in these stages. Thrombin is a clotting effecter enzyme, having many biologically important functions such as the activation of platelets, conversion of fibrinogen to a fibrin network, and feedback amplification of coagulation. The coagulation cascade can be generalized as three pathways: an intrinsic pathway, an extrinsic pathway, and a common pathway. The intrinsic pathway may be triggered by surface contact, while the extrinsic pathway may be triggered by tissue/cell defect. Both can lead to the formation of thrombin, which is the common pathway. Thrombin converts the fibrinogen into fibrin, and then the fibrin may form a cross-linked fibrin meshwork.

Figure 4:
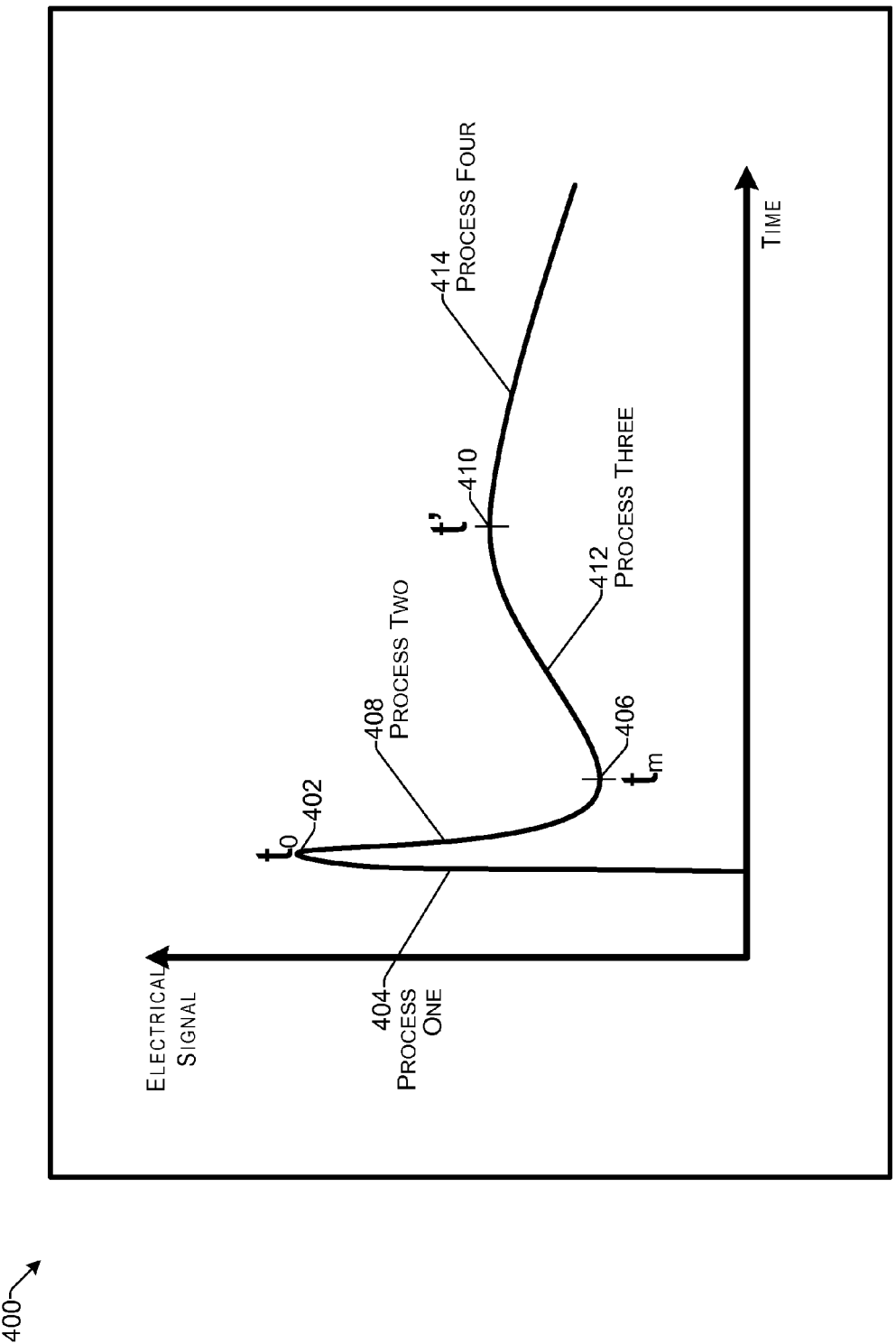
FIG. 4 illustrates an example measurement function of time according to some implementations.

FIG. 4 illustrates an exemplary curve 400 of the measurement function of the electrical signal when plotted against time according to some implementations. The curve 400 of FIG. 4 is illustrated only as an example. The electrical signal detected by the device 302 may be an electrical potential difference (voltage) or a current. The measurements whose time function is used for coagulation analysis either may be the same as the actually detected electrical signal, or may be based on another property derived from the detected electrical signal, such as resistance or impedance. In some cases, the measurement function may be analyzed by the processor 316 of the device 102 mathematically or computationally without actually generating or plotting a visible curve 400 of the electrical signal when determining an accumulative property of the curve 400.

When the blood sample 104 is deposited in the sample receptacle 212, the blood is carried forward by a capillary action to reach the reaction area 204, as discussed above. In the example discussed above, the reaction area 204 contains multiple electrodes, which may apply an electrical potential difference across the blood sample 104 in the reaction area 204. In some examples, the electrical potential difference may be a constant voltage applied by the device 302 to the electrodes 214. In other examples, the voltage or current may be varied, the current may be an alternating current, or the like.

In some implementations, the electrical signal detected at an output terminal, such as first electrode 216 or second electrode 220, is the electrical current that passes through the blood sample in the reaction area 204, or an electrical current that is related to the electrical current that passes through the blood sample. The curve 400 of FIG. 4 illustrates an example of the behavior of the current response (i.e., the electrical signal) due to the coagulation reaction in the blood sample, which may have also reacted with one or more reagents 208.

In the example of FIG. 4, the current is shown by the curve 400 to have increased rapidly at first to reach a first peak 402 at time $t_0$. This result may be attributed to the blood sample forming an electrical connection between opposing electrodes, e.g., the first electrode 216 and the second electrode 220. The time point $t_0$ may be the time at which the electrodes make a complete electrical connection through the blood sample. The process during the time span from the initial time to the first peak 402 at time $t_0$ is referred to as process one 404 in this example.

After time $t_0$, the current starts to drop. This result may be attributed to a process of fibrinogen being converted to fibrin to form insoluble products. This process may also be accompanied by the clotting cascade being activated, which leads to thrombin production. The curve 400 shows a drop in current passed through the blood sample as this activity takes place until a first bottom 406 of the curve 400 is reached at a time $t_m$. The process from the first peak 402 at time $t_0$ to the first bottom 406 at time $t_m$ of the curve 400 is referred to as process two 408 in this example.

From time $t_m$ at the first bottom 406 of the curve 400, the current then starts to gradually increase again to reach a second peak 410 at time t', which may be a result of a process of fibrinogen changing to fibrin under the catalysis of thrombin and further starting to form small particles. The process from the first bottom 406 at time $t_m$ to the second peak 410 at time t' is referred to as process three 412 in this example.

After the second peak 410 at time t', the current begins to go down again slightly (or may remain steady in some cases). This process may be due to mesh formation of fibrin, accompanied by the sedimentation of fibrin. The process following time t' at the second peak 410 is referred to as process four 414 in this example.

Example Accumulative Properties

Conventional examples of prothrombin time determination (such as PT monitoring) may be based upon an end-state determination using slope calculation. However, this technique is not suitable for the other types of anticoagulation monitoring, such as heparin dosage monitoring.

Disclosed herein is a new technique for coagulation monitoring, which may be referred to as the Residual Accumulative Conductive Energy (RACE) method. According to the RACE method disclosed herein, the curve 400 of the measurement function (e.g., the measured electrical signal) may be divided or segmented according to the four processes 404, 408, 412 and 414, as discussed above with respect to FIG. 4. The method uses RACE as an empirical accumulative property of the time function of the measurements of the electrical signal. The computed value of RACE may be used to estimate a coagulation characteristic, rather than the conventional technique of end-state determination such as based on slope calculation.

Figure 5:
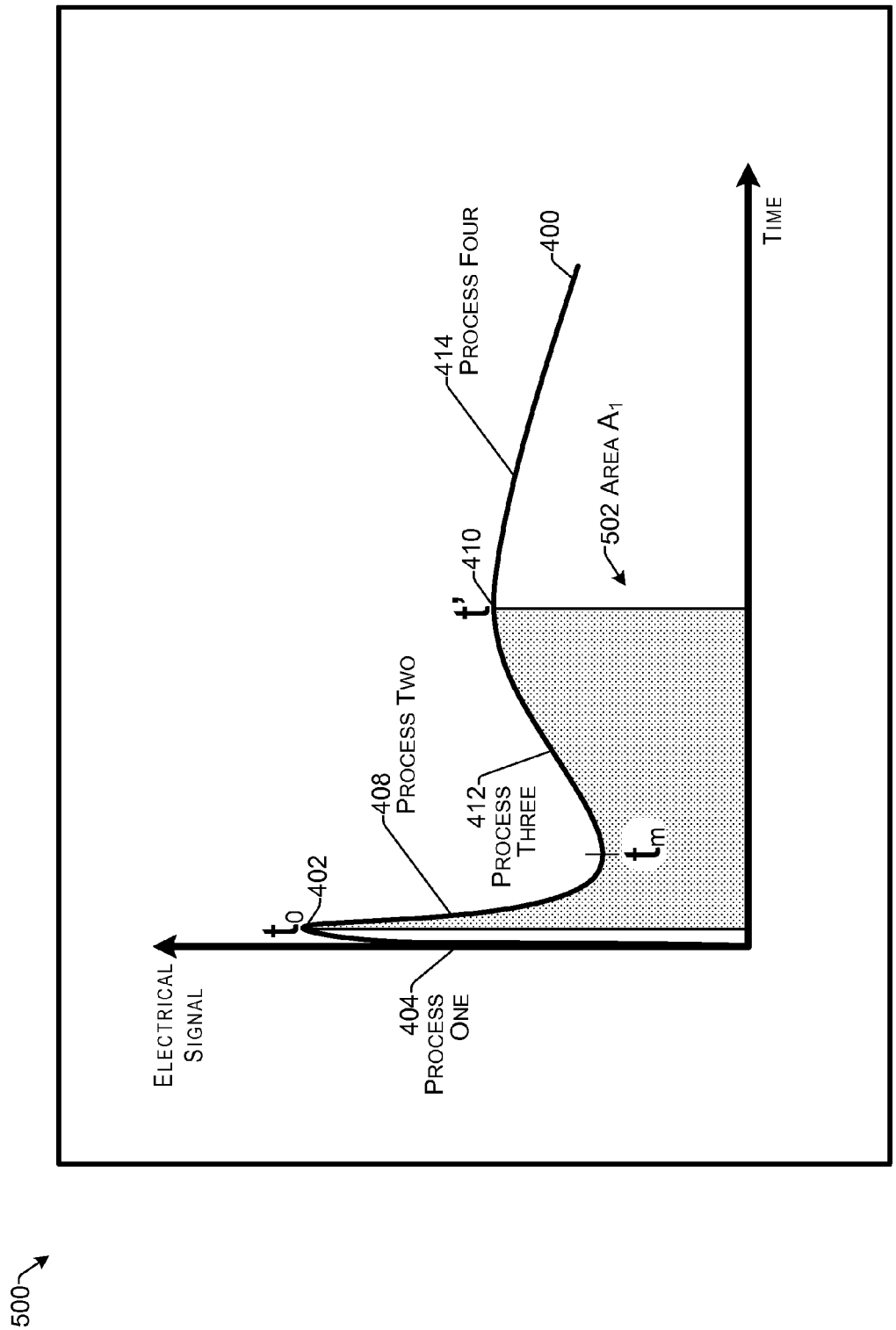
FIG. 5 illustrates an example accumulative property of the measurement function according to some implementations.
Figure 6:
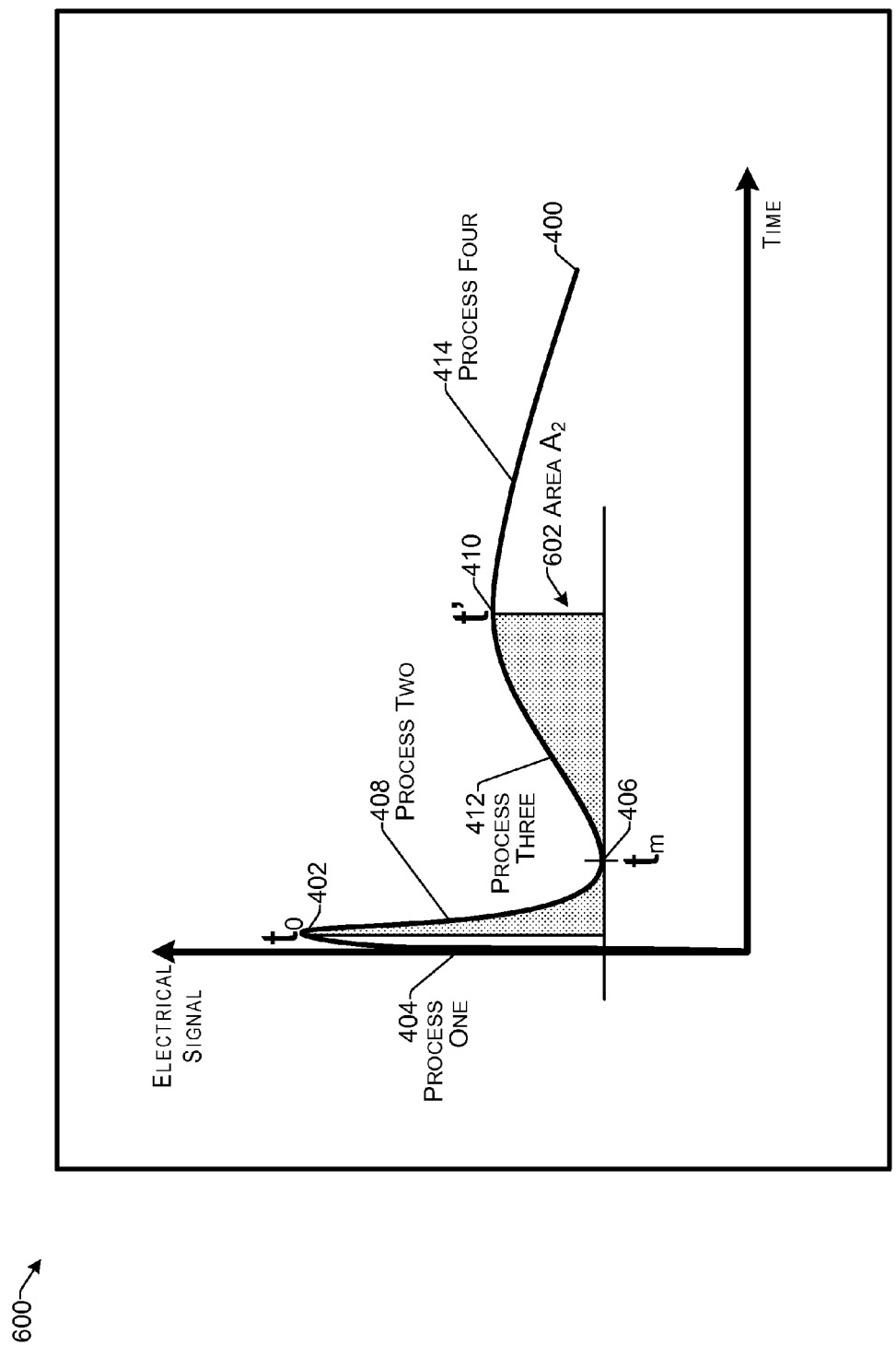
FIG. 6 illustrates an example accumulative property of the measurement function according to some implementations.

FIGS. 5 and 6 illustrate examples of using RACE for coagulation monitoring according to some implementations. In these examples, RACE is applied as a function of an area under the signal curve 400 from time $t_0$ to time t', i.e., from the first peak 402 to the second peak 410. Based upon the analysis of the measurement function (e.g., the function of the electrical signal over time), the implementations herein may determine the blood clotting time based upon the data accumulated during process two 408 and process three 412. $RACE_{clotting}$ is an exemplary accumulative property of the measurement function aiming to correlate with a coagulation characteristic such as PT, ACT and/or APTT.

FIG. 5 illustrates an example 500 of a first area $A_1$ 502 that may be determined based on a segment of the curve 400 from time $t_0$ to time t' according to some implementations. For example, the first area $A_1$ 502 may be determined as an integral of an area under the curve 400 from time $t_0$ to time t', i.e., from the first peak 402 to the second peak 410.

FIG. 6 illustrates an example 600 of a second area $A_2$ 602 that may be determined based on a segment of the curve 400 from time $t_0$ to time t' according to some implementations. For example, the second area $A_2$ 602 may be determined as an integral of the area under the curve 400 from time $t_0$ to time t' by integrating a difference between the variable values and a fixed minimum value (at time $t_m$) at the first bottom 406 of the curve 400 of the current over the characteristic time period.

$RACE_{clotting}$ may be empirically determined according to the following equation:

$$RACE_{clotting} = (t'-t_0)^n \times (A_1)^m / (A_2)^p \quad \text{Equation 1}$$

$RACE_{clotting}$ represents an accumulated change of a coagulation process. The time t' is the time at which the blood sample begins sedimentation of fibrin, and the time $t_0$ is the time at which the electrodes and the blood sample in the reaction area 204 are electrically connected. The area $A_1$ is the first integrated area 502 computed by integrating variable values of the electrical current from time $t_0$ to time t', which is a characteristic time period within the measurement time duration. Accordingly, the area $A_1$ represents a total residual conductive energy accumulated during the process two 408 and the process three 412. The area $A_2$ is the second integrated area computed by integrating a difference between the variable values and a fixed minimum value (at time $t_m$) of the current over the characteristic time period, which in this case is the time from time $t_0$ to time t'.

Power indexes n, m and p are empirical parameters. Experiments have shown that setting the empirical parameters n, m and p substantially close to 1, 1, and ½, respectively, can result in relatively good correlation between $RACE_{clotting}$ and one or more commonly used coagulation characteristics such as PT, ACT or APTT.

Further, this disclosure is not limited to the particular formula described above with respect to Equation 1, nor is this disclosure limited to particular values of the empirical parameters n, m and p, which may be preferable for certain applications.

As one example application, four components of the clotting cascade are dependent on vitamin K content. These four components are tissue thromboplastin (Factor II, TF), factor IX, factor X and prothrombin. Warfarin is an oral anticoagulant medication, widely used for the prevention of thromboembolic events, including deep venous thrombosis, pulmonary embolism, myocardial infarction and stroke. Warfarin is a vitamin K analogue and therefore warfarin therapy targets these elements of the clotting cascade, which has a largest impact on the extrinsic pathway. Warfarin does not have direct anticoagulant properties, but exerts its effects by inhibiting vitamin K pathway dependent clotting factors II, VII, IX, X, and the antithrombotic proteins C and S.

The Prothrombin Time (PT) test may be used to assess the extrinsic and common pathway clotting systems and for monitoring long-term anticoagulation therapy. Accordingly, implementations herein may use $RACE_{clotting}$ as discussed above to determine a Prothrombin Time (PT) test results for wafarin monitoring, wherein $RACE_{clotting}$ is calculated by the Equation 1. For example, a suitable reagent 208 may be used for PT testing by taking a plurality of measurements of an electrical signal passed through a blood sample introduced to the reagent. The accumulated property may be determined using the $RACE_{clotting}$ technique discussed above, and the PT test results may be determined based on the $RACE_{clotting}$ results.

Figure 7:
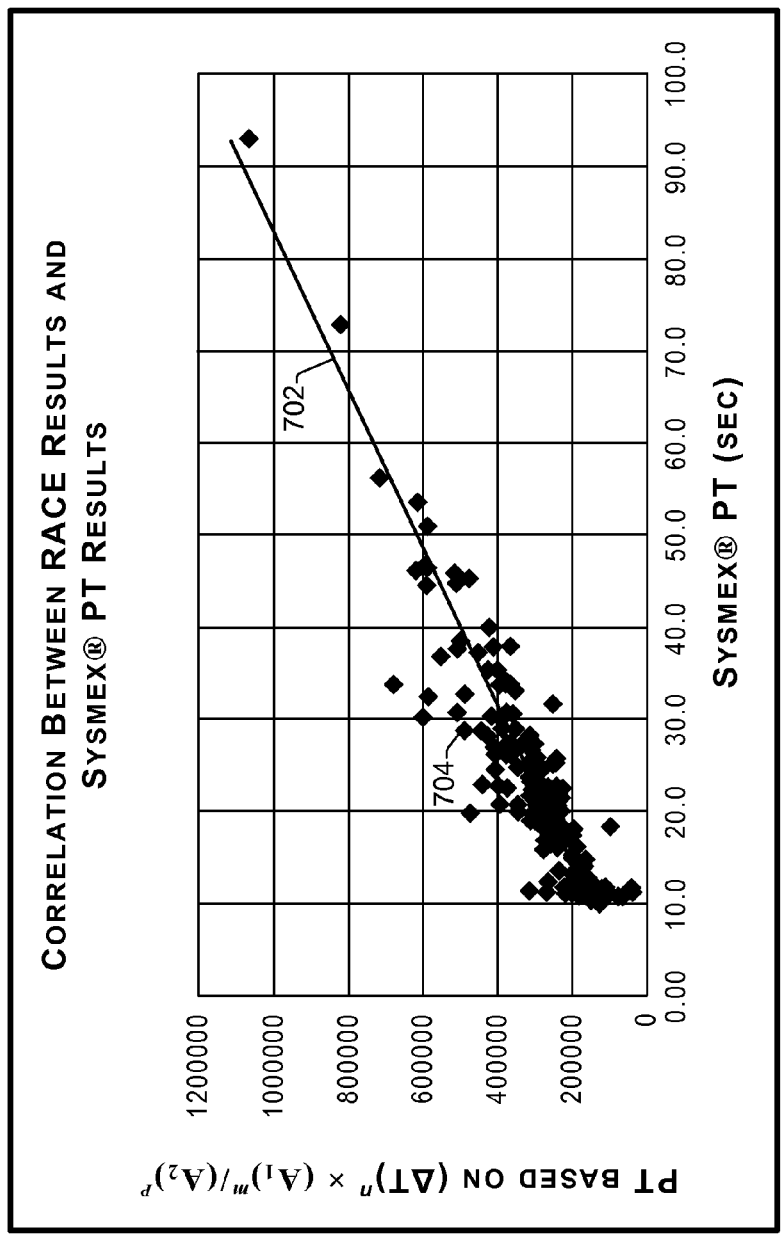
FIG. 7 illustrates an example of correlation between RACE results and reference lab system results for PT testing according to some implementations.

FIG. 7 shows an example 700 of a correlation between the $RACE_{clotting}$ results based on Equation 1 described above and PT obtained by using a reference lab system, namely a Sysmex® CA-7000 System, available from Siemens AG, Erlangen, Germany. The data in FIG. 7 is exemplary of data collected in hospitals using qLabs® ElectroMeters (Model Q-1) and qLabs® PT-INR strips (both from Micropoint Biotechnologies, Inc. of Shenzhen, China) modified to meet the need of the RACE technique as described in this invention. The illustrated example is based on data collected from 233 patients. For each patient, a drop of finger stick capillary blood less than 10 μL was used for RACE technique, while a tube of citrated venous blood was collected for the Sysmex® reference lab system from the same patient within 30 min of the RACE test.

As illustrated in FIG. 7, line 702 represents the best-fit line of the experimental results as represented with a plurality of diamonds 704 for PT in a range of 9.7-92.9 seconds. In this example, the line 702 may be expressed as y=11691x+30983 and the correlation coefficient R=0.92. The results show that there is a sufficient correlation between the $RACE_{clotting}$ results and the results of the Sysmex® PT results, such that the $RACE_{clotting}$ results may be used to obtain PT test results.

The $RACE_{clotting}$ technique disclosed herein may also be used for heparin monitoring. Heparin is a common medication connected with cardiac bypass surgery, cardiac catheterization, renal dialysis, and in critical care situations for acute myocardial infarction. Treatment with heparin causes the inactivation of thrombin. Heparin exerts an anticoagulation effect by binding to and forming a complex with a plasma cofactor called antithrombin III.

Accordingly, the $RACE_{clotting}$ technique discussed above may be employed to monitor heparin in blood, such as by including the reagent thrombin as the reagent 208 on the cartridge 202. In some examples herein, the $RACE_{clotting}$ technique may even result in a wider signal detection range than conventional methods and detection of heparin concentrations lower than 1 U/ml. Thus, the accumulative property discussed above with respect to FIGS. 5 and 6 may provide a close correlation with heparin concentration in a blood sample, and may be correlated as an APTT or ACT test result and/or used as such. Conventionally, heparin concentrations lower than 1.5 U/mL are often monitored by APTT, while heparin concentrations higher than 1.5 U/mL are often monitored by ACT.

Figure 8:
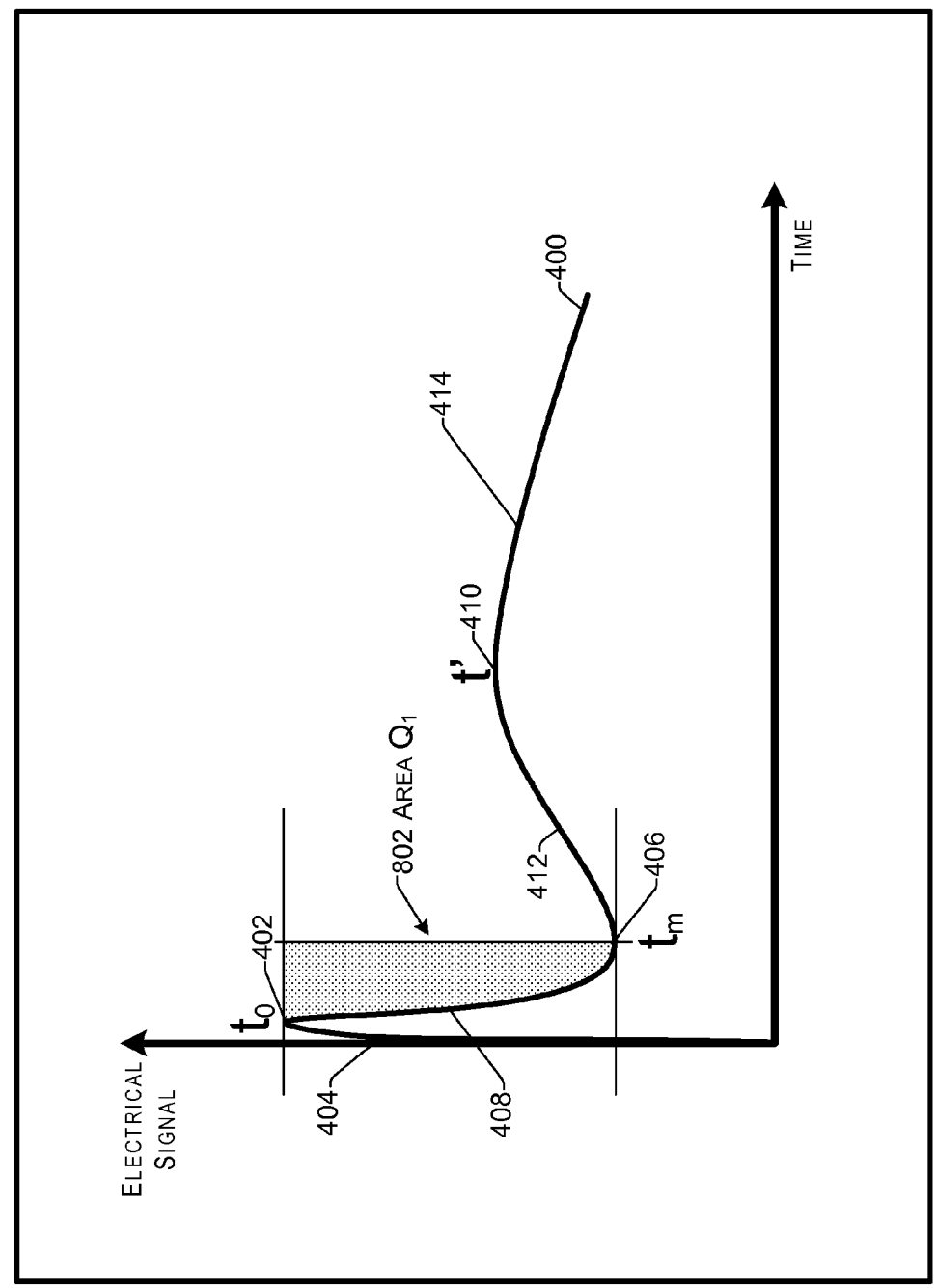
FIG. 8 illustrates an example accumulative property of the measurement function according to some implementations.
Figure 9:
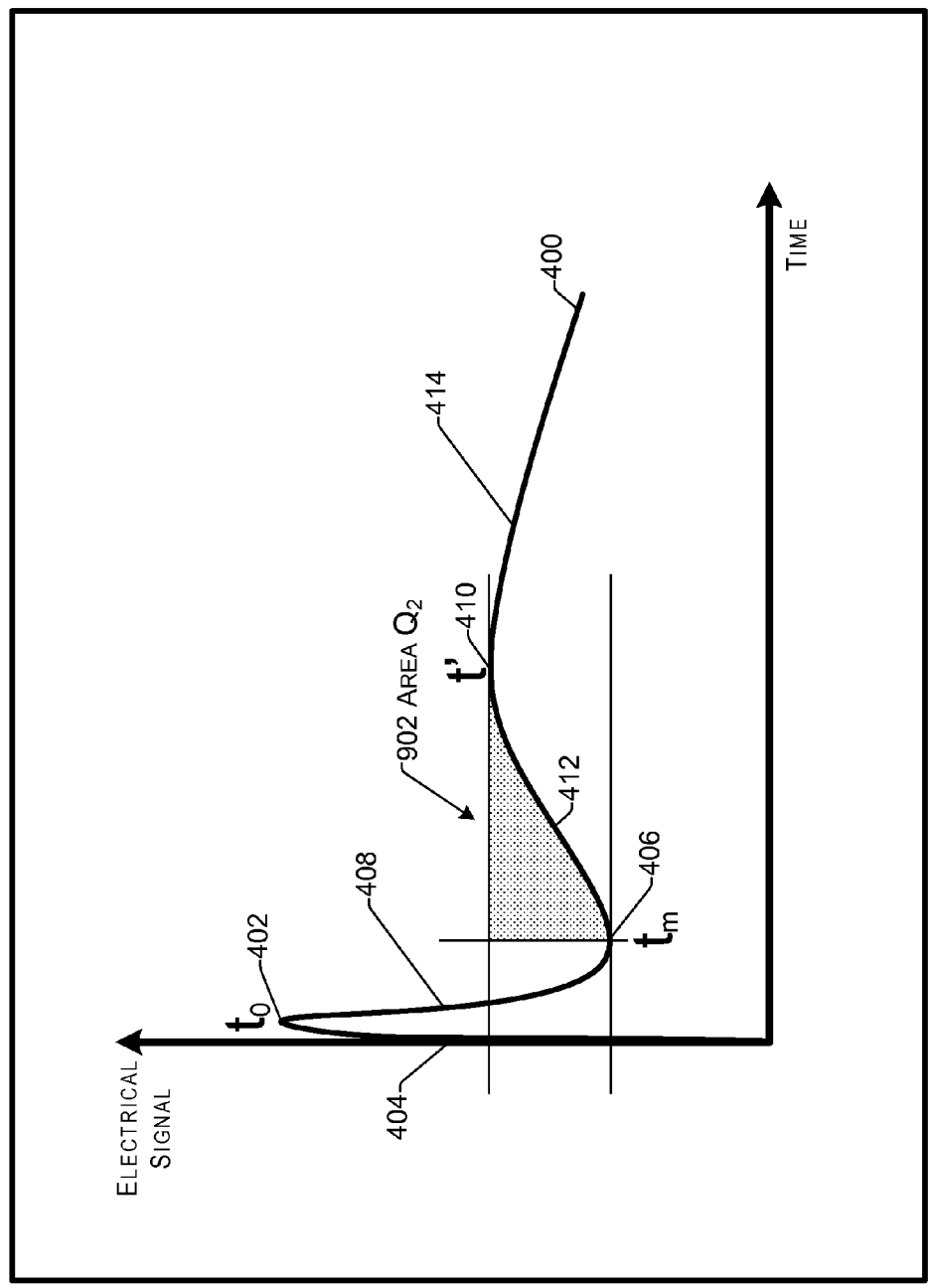
FIG. 9 illustrates an example accumulative property of the measurement function according to some implementations.

FIGS. 8-9 illustrate another example of using RACE for coagulation monitoring and testing according to some implementations. In the examples of FIGS. 8-9, RACE is applied as a function of one or more areas corresponding to a segment of the signal curve 400 from time $t_0$ to time t', i.e., from the first peak 402 to the second peak 410. Based upon the analysis of the measurement function (e.g., the function of the electrical signal over time), the implementations herein may determine the blood clotting characteristic based upon the data accumulated during process two 408 and process three 412. The RACE technique in this example is an exemplary accumulative property of the measurement function aiming to correlate with a coagulation characteristic such as TT and/or APTT.

FIG. 8 illustrates an example 800 of a first area $Q_1$ 802 that may be determined in relation to the curve 400 from time $t_0$ to time $t_m$ according to some implementations. For example, the first area $Q_1$ 802 may be determined as an integral of the curve 400 from time $t_0$ to time $t_m$, i.e., the segment of the curve from the first peak 402 to the first bottom 406 of the curve 400, and in which the area $Q_1$ 802 is bounded by the first peak 402 and the time $t_m$.

FIG. 9 illustrates an example 900 of a second area $Q_2$ 902 that may be determined in relation to a segment of the curve 400 from time $t_m$ to time t' according to some implementations. For example, the second area $Q_2$ 902 may be determined as an integral of the curve 400 from time $t_m$ to time t', i.e., the segment of the curve from the first bottom 406 to the second peak 410 of the curve 400, and in which the area $Q_2$ 902 is bounded by the time $t_m$ and the second peak 410.

The areas $Q_1$ 802 and $Q_2$ 902 may be used for correlation with tests such as TT or APTT. For example, a first suitable reagent 208, such as thromboplastin, may be used for correlation with APTT testing by taking a plurality of measurements of an electrical signal passed through a blood sample introduced to the first reagent. A different, second suitable reagent 208, such as thrombin, may be used for correlation with TT testing by taking a plurality of measurements of an electrical signal passed through a blood sample introduced to the second reagent. The following equation may be used for correlation with either or both of APTT and TT testing.

$RACE_{APTT}$ or $RACE_{TT}$ may be empirically determined according to the following equation:

$$RACE_{APTT} \text{ or } RACE_{TT} = kQ, \text{ where } Q = Q_1 + Q_2 \qquad \text{Equation 2}$$

$RACE_{APTT}$ or $RACE_{TT}$ represents an accumulated change of a coagulation process. The area $Q_1$ is the first integrated area 802 computed by integrating variable values of the electrical current from time $t_0$ to time $t_m$, which is a characteristic time period within the measurement time duration. Accordingly, the area $Q_1$ represents a total residual conductive energy accumulated during the process two 408. The area $Q_2$ is the second integrated area 902 computed by integrating variable values of the electrical current from time $t_m$ to time t', which is another characteristic time period within the measurement time duration. Accordingly, the area $Q_2$ represents a total residual conductive energy accumulated during the process three 412.

Constant k may be an empirical parameter. Experiments have shown that setting the empirical parameter k substantially close to 1 can result in substantial correlation between $RACE_{APTT}$ and/or $RACE_{TT}$ and one or more commonly used coagulation characteristics such as APTT or TT, respectively. Further, this disclosure is not limited to the particular formula described above with respect to Equation 2, nor is this disclosure limited to particular values of the empirical parameter k, which may be preferable for certain applications.

Figure 10:
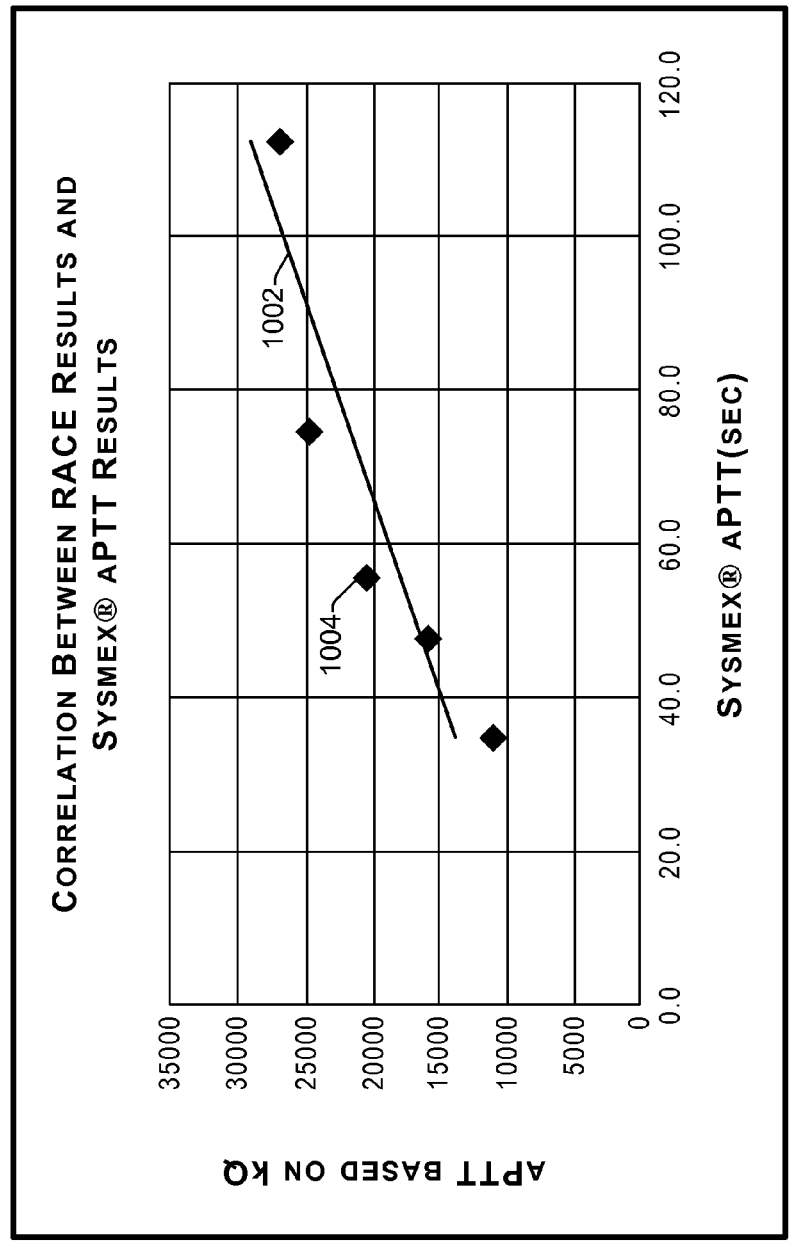
FIG. 10 illustrates an example of correlation between RACE results and reference lab system results for APTT testing according to some implementations.

FIG. 10 illustrates an example 1000 of correlation between RACE results based on Equation 2 and Sysmex® APTT results for 5 samples. Similar to the example 700 discussed above with respect to FIG. 7, using a modified qLabs® ElectroMeter and qLabs® PT-INR strips, five samples were tested and Equation 2 was applied to obtain APTT test results with the RACE technique. For instance, five venous blood samples were drawn without anticoagulant, each spiked with a different concentration of heparin and tested with both the RACE technique described herein and a reference lab system, namely a Sysmex® CA-500, available from Siemens AG of Erlangen, Germany. In the illustrated example, the line 1002, expressed as y=194.06x+7275.1 for APTT in the range of 34.6-112.3 seconds, is the best fit line of the experimental data points as represented with diamonds 1004. The correlation coefficient is R=0.91 in this example, which shows sufficient correlation for the RACE results for providing APTT testing results.

Figure 11:
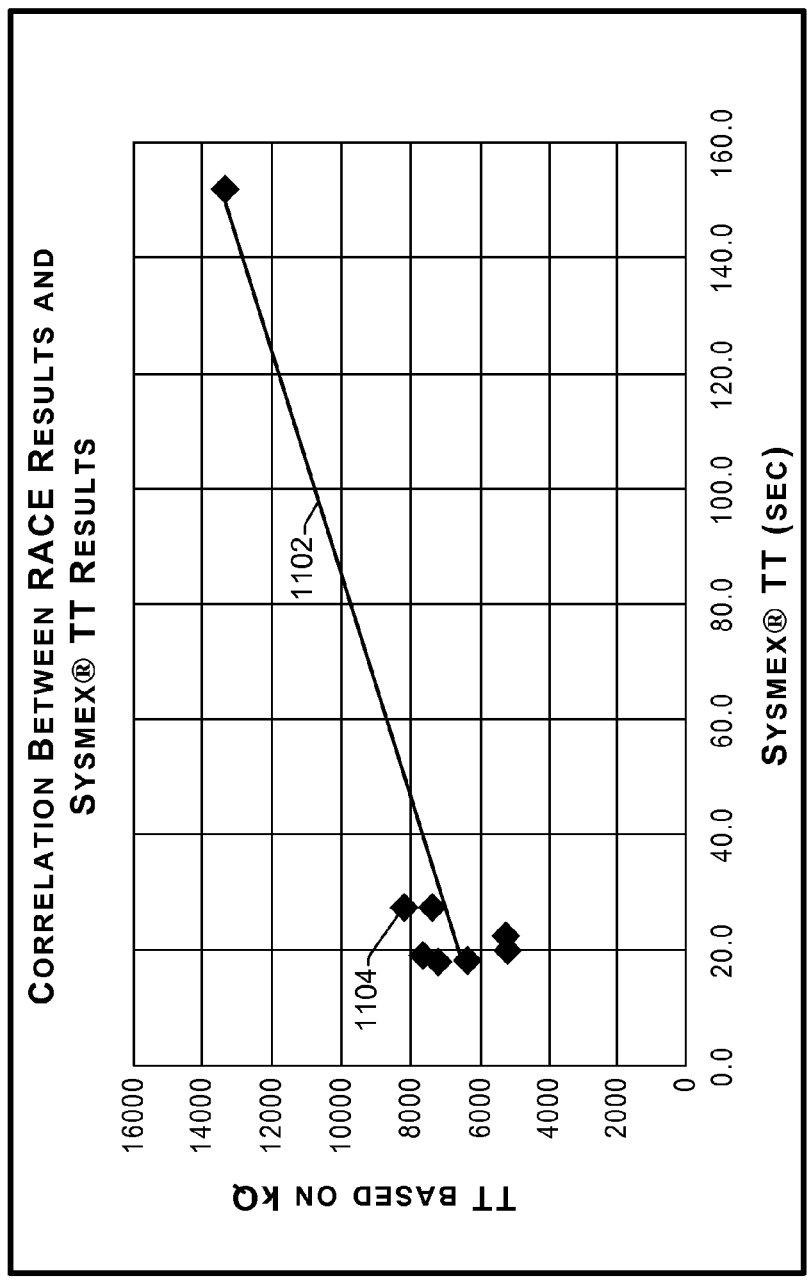
FIG. 11 illustrates an example of correlation between RACE results and reference lab system results for TT testing according to some implementations.

TT measures the conversion of fibrinogen to fibrin. As one example, this test may be performed by the addition of purified thrombin to patient plasma. The resulting clotting time is a function of fibrinogen concentration and activity. The TT may be used as a screening test for the presence of heparin in a plasma sample. Other causes for a prolonged TT include quantitative deficiency of fibrinogen, qualitative abnormality of fibrinogen (dysfibrinogen), elevated levels of fibrin degradation products (FDP), the presence of certain paraproteins, and markedly increased levels of fibrinogen. FIG. 11 illustrates an example 1100 of correlation between RACE results based on Equation 2 and Sysmex® TT results for eight samples using a Sysmex® CA-500 as a reference lab system. Each of the eight samples was spiked with a different concentration of heparin and tested using both the RACE technique of Equation 2 and the Sysmex® CA-500 reference lab system. In the illustrated example, the line 1102 indicates the best-fit line of the experimental data points as represented with the diamonds 1104. The line 1102 may be represented as y=51.503x+5629.5 for TT in the range of 19-152 seconds. The correlation coefficient R=0.92, which is sufficient to correlate the $RACE_{TT}$ results to provide TT testing results.

In addition to using the above-described RACE techniques of Equation 1 and Equation 2 to characterize the coagulation changes in a blood sample, additional RACE techniques herein may be used for determining blood coagulation characteristics, such as fibrinogen content (FIB). For determining FIB characteristics, a different accumulative property of the measurement function may be empirically derived, which is denoted herein as $RACE_{FIB}$, for satisfactory correlation with FIB measurement.

Fibrinogen is acted upon by thrombin to produce fibrin monomers that polymerize to form fibrin strands, and ultimately a fibrin clot. Not all fibrinogen molecules are capable of participating in clot formation, and only clottable fibrinogen is of interest for the purpose of hemostasis screening. Fibrinogen assays available on current automated coagulation analyzers include the Clauss and PT-derived methods. In some cases, PT, APTT and platelet assays are sufficient for screening bleeding patients. However, in cases where fibrinogen levels may drop precipitously (e.g., disseminated intravascular coagulation in obstetric patients), a fibrinogen assay may be used as a screening test, since the PT and APTT tests are relatively insensitive to low levels of fibrinogen.

Figure 12:
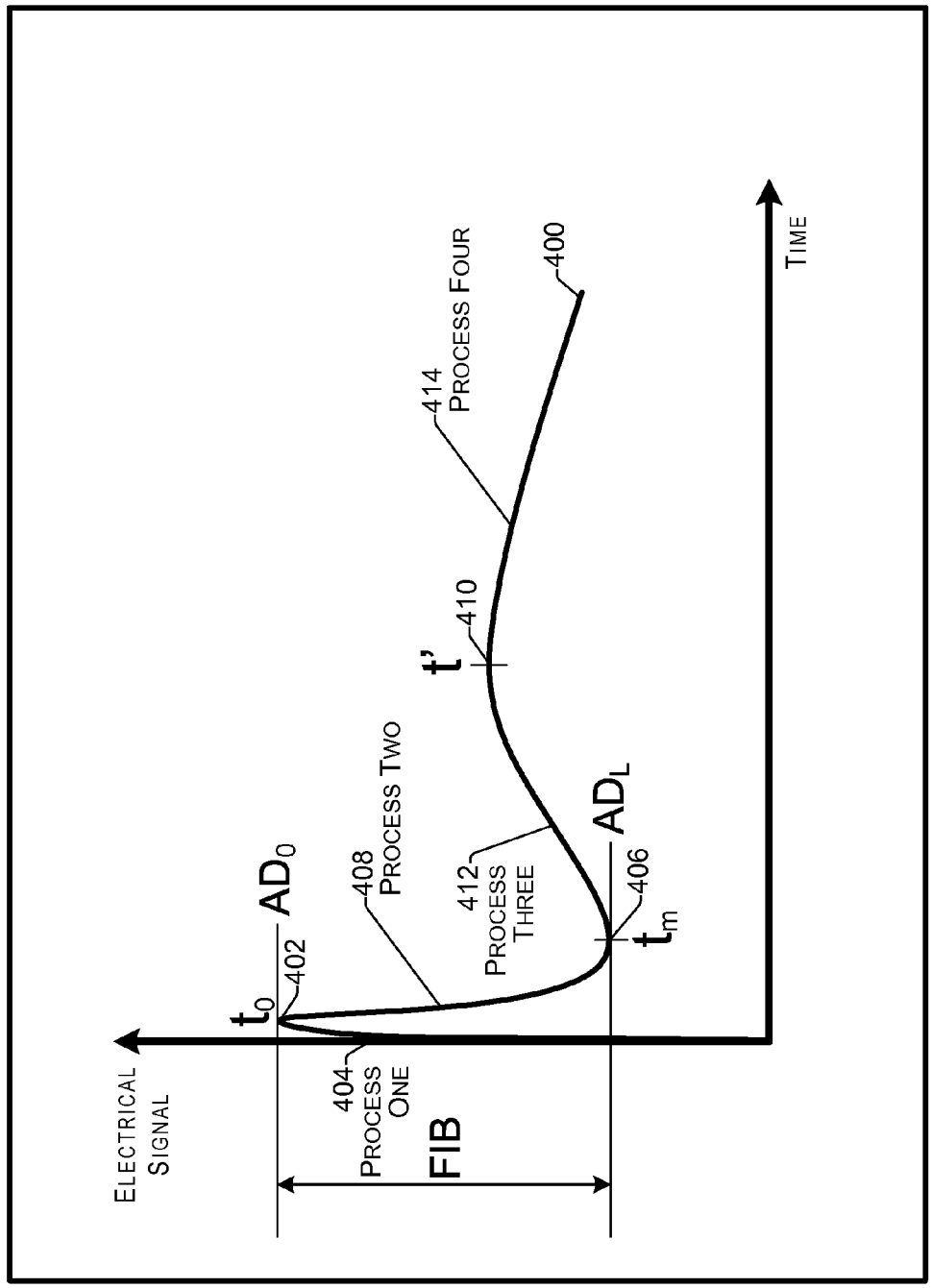
FIG. 12 illustrates an example accumulative property of the measurement function according to some implementations.

FIG. 12 illustrates an example 1200 of using RACE to determine FIB in a blood sample according to some implementations. In this example, a first amplitude $AD_0$ is the amplitude of the curve 400 at the first peak 402 at time $t_0$ and a second amplitude $AD_L$ is the amplitude of the curve 400 at the first bottom 406 at time $t_m$. The $RACE_{FIB}$ may be expressed by the following equation:

$$RACE_{FIB} = (AD_0 - AD_L)^r \quad \text{Equation 3}$$

Thus, the $RACE_{FIB}$ is an accumulated value of the process two 408, that uses the difference in amplitude $AD_0$ (the electrical signal amplitude at the first peak 402 at time $t_0$) and $AD_L$ (the electrical signal amplitude at the first bottom 406 at time $t_m$) and which represents the process of fibrinogen converting to fibrin. The power index r in Equation 2 is an empirical parameter, which may be 1 or close to 1. The results of the $RACE_{FIB}$ equation may be correlated to fibrinogen content in a blood sample. For example, the blood sample may be prepared for measuring fibrinogen content, the electrical signal may be measured over time, and the accumulative property, $RACE_{FIB}$, can be correlated to the fibrinogen content of the blood sample.

Figure 13:
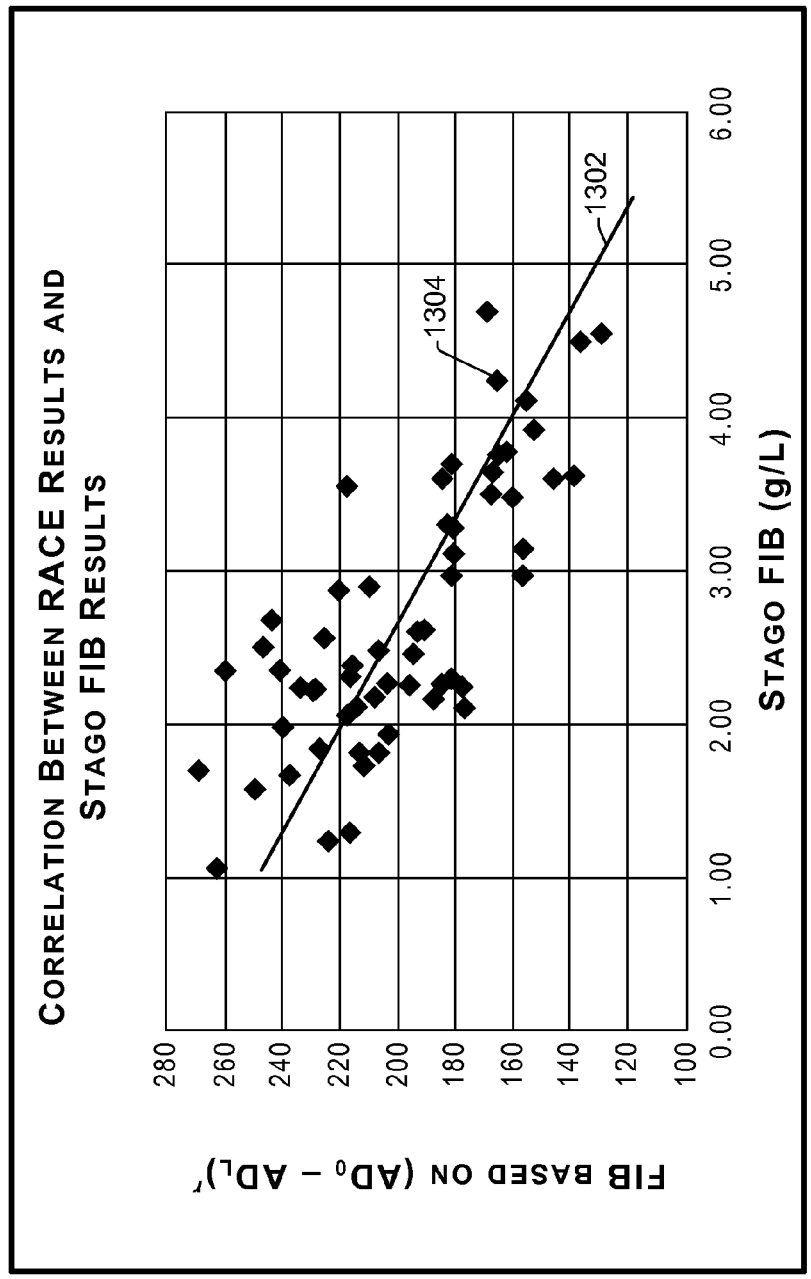
FIG. 13 illustrates an example of correlation between RACE results and reference lab system results for FIB testing according to some implementations.

FIG. 13 illustrates an example 1300 of a correlation between the $RACE_{FIB}$ technique herein and FIB testing according to some implementations. Samples were obtained from 60 patients and tested using both the $RACE_{FIB}$ technique and a reference lab system, namely a Stago Analyzer available from Diagnostica Stago, Inc., of Parsippany, N.J. In the example of FIG. 13, the line 1302, expressed as y=−29.22x+277.3 for FIB in the range of 1.03 to 4.69 g/L, is the best fit line of the experimental data points as represented with the diamonds 1304. The correlation coefficient R=0.76 indicates sufficient correlation to obtain FIB test results based on the $RACE_{FIB}$ technique.

Exemplary implementations are employed to illustrate the concept and implementation of the present invention in this disclosure. The exemplary implementations are only used for better understanding of the method and core concepts of the present invention. Based on the concepts in this disclosure, a technician of ordinary skill in the art may make some modifications. These modifications should also be under the scope of the present invention.

Example Processes

Figure 14:
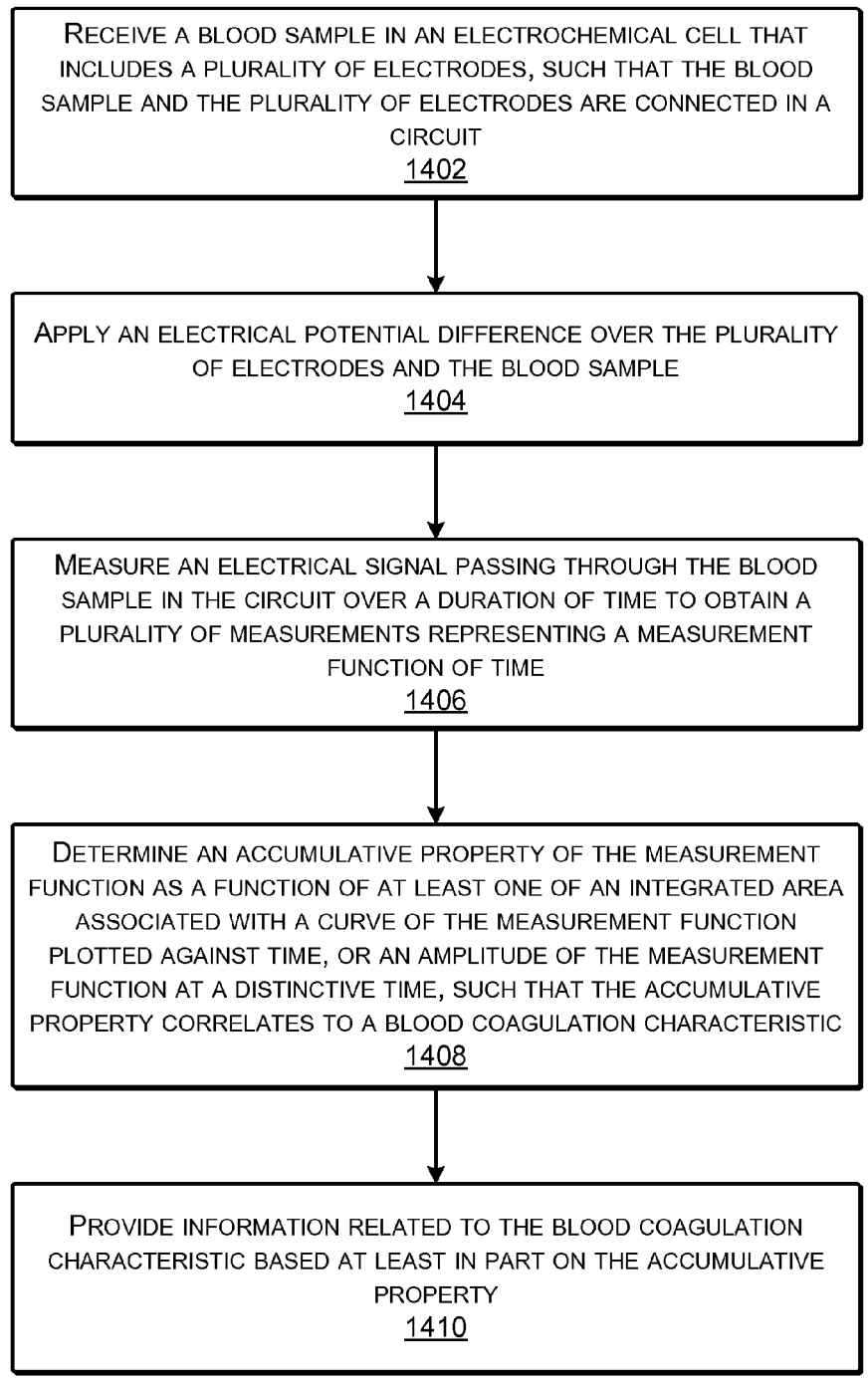
FIG. 14 is a flow diagram illustrating an example process for testing a blood coagulation characteristic according to some implementations.
Figure 15:
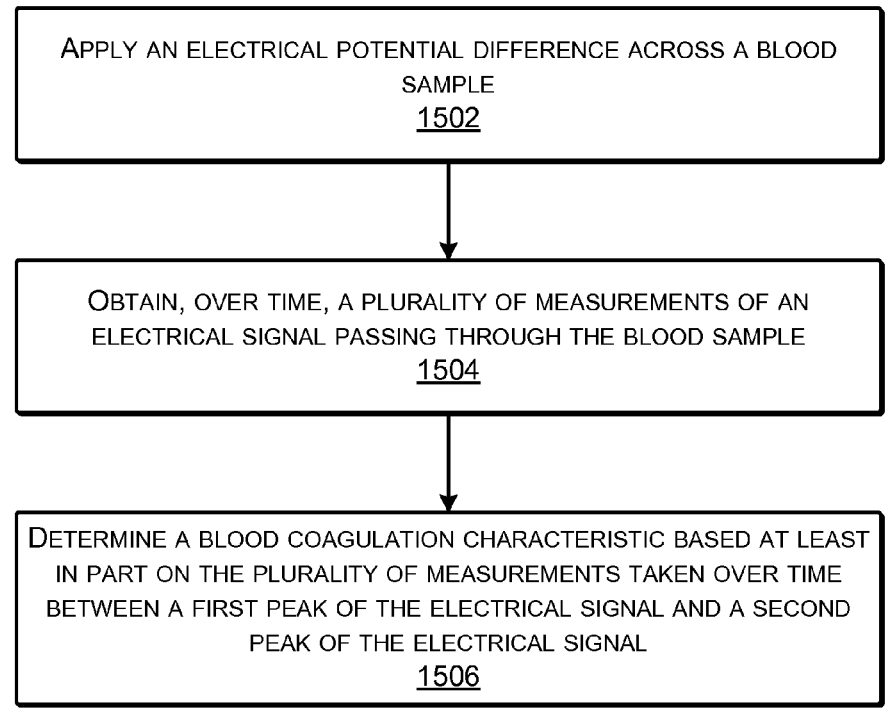
FIG. 15 is a flow diagram illustrating an example process for testing a blood coagulation characteristic according to some implementations.

FIGS. 14-15 illustrate example processes according to some implementations. These processes, as well as the other processes described herein, are illustrated as a collection of blocks in logical flow diagrams, which represent a sequence of operations, some or all of which can be implemented in hardware, software or a combination thereof. In the context of software, the blocks may represent computer-executable instructions stored on one or more computer-readable media that, when executed by one or more processors, perform the recited operations. Generally, computer-executable instructions include routines, programs, objects, components, data structures and the like that perform particular functions or implement particular abstract data types. The order in which the operations are described should not be construed as a limitation. Any number of the described blocks can be combined in any order and/or in parallel to implement the process, or alternative processes, and not all of the blocks need to be executed. For discussion purposes, the processes are described with reference to the architectures, environments and frameworks described in the examples herein, although the processes may be implemented in a wide variety of other architectures, environments or frameworks.

FIG. 14 is a flow diagram illustrating an example process 1400 for testing a blood coagulation characteristic that may be executed by a device according to some implementations.

At 1402, the device receives a blood sample in an electrochemical cell that includes a plurality of electrodes such that the blood sample and the plurality of electrodes are connected in a circuit. For example, a blood sample may be deposited into a cartridge or reagent strip, and the cartridge or reagent strip may be inserted into a device capable of measuring one or more characteristics of the blood sample.

At 1404, the device applies an electrical potential difference over the plurality of electrodes and the blood sample. For example, the device may pass an electrical current through the blood sample.

At 1406, the device measures an electrical signal passing through the blood sample in the circuit over a duration of time to obtain a plurality of measurements representing a measurement function of time. For example, the device may measure the current passing through the blood sample over a period of time to detect changes in the current such as changes in an amplitude of the current over time.

At 1408, the device determines an accumulative property of the measurement function as a function of at least one of an integrated area calculated based on a curve of the measurement function plotted against time, or an amplitude of the measurement function at a distinctive time, such that the accumulative property correlates to a blood coagulation characteristic. For example, the device may apply an accumulative property that correlates to a blood coagulation characteristic. In some cases, the accumulative property may be based at least in part on determining an area corresponding to a segment of a curve of the electrical signal measurements plotted over time. In other cases, the accumulative property may be based at least in part on determining a difference in amplitude of a segment of the curve the electrical signal measurements plotted over time.

At 1410, the device provides the blood coagulation characteristic based at least in part on the accumulative property. For example, the device may determine the blood coagulation characteristic that correlates to the accumulative property, and may provide information related to this blood coagulation characteristic, such as by displaying the information on a display, storing the information to a computer readable medium, and/or sending the information to a computing device.

FIG. 15 is a flow diagram illustrating an example process 1500 for testing a blood coagulation characteristic that may be executed according to some implementations.

At 1502, a device applies an electrical potential difference across a blood sample. For example, the device may apply an electrical potential difference across a blood sample to pass an electrical current through the blood sample.

At 1504, a test device obtains, over time, a plurality of measurements of an electrical signal passing through the blood sample. For example, the device may measure changes in an electrical current that passes through the blood sample over a period of time.

At 1506, the test device determines a blood coagulation characteristic based at least in part on the plurality of measurements taken over time between a first peak of the electrical signal and a second peak of the electrical signal. For example, the test device may correlate an area calculated based on a segment of a curve of the electrical signal to a blood coagulation characteristic. For instance, the curve segment may extend from a first peak to a second peak of the curve. Alternatively, the test device may correlate a change in an amplitude of a curve segment of the electrical signal to a different blood coagulation characteristic. For instance, the curve segment may extend from the first peak to the first bottom of the curve.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, implementations herein are not limited to the particular examples shown and discussed.

This disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

The invention claimed is:

1. A device comprising:
a sample cartridge receiver to receive a sample cartridge including a sample receptor;
a circuit to connect to a blood sample delivered to the sample receptor of the sample cartridge, such that at least part of the blood sample and a plurality of electrodes are connected in the circuit;
one or more processors; and
computer-readable media storing executable instructions, which when executed, cause the one or more processors to perform operations comprising:
causing an electrical potential difference to be applied over the plurality of electrodes and the at least part of the blood sample;
receiving, over a duration of time, measurements of an electrical signal passing through the blood sample in the circuit to obtain a plurality of measurements;
generating a measurement function of time from the plurality of measurements, the measurement function having a first peak, a first bottom, and a second peak;
determining an accumulative property of the blood sample based at least in part on the measurement function of time, wherein:
(a) the accumulative property is Prothrombin Time (PT) and a PT value is determined at least in part by a ratio of (i) an area under the measurement function of time, above a zero value of the electrical signal, and between the first peak and the second peak and (ii) an area under the measurement function of time, above a value of the electrical signal at the first bottom, and between the first peak and the second peak;
(b) the accumulative property is Activated Partial Thromboplastin Time (APTT) or Thrombin Time (TT) and an APTT value or TT value is determined at least in part by a summation of (i) an area between the first peak and the first bottom that is above the measurement function of time and below a value of the electrical signal at the first peak and (ii) an area between the first bottom and the second peak that is above the measurement function of time and below a value of the electrical signal at the second peak; or
(c) the accumulative property is fibrinogen content (FIB) and a FIB value is determined at least in part by a difference between a value of the electrical signal at the first peak and a value of the electrical signal at the first bottom.

2. The device as recited in claim 1, wherein the blood sample is delivered through a sample delivery channel comprising a microfluidic channel.

3. The device as recited in claim 1, wherein the accumulative property correlates to a blood coagulation characteristic.

4. The device as recited in claim 3, wherein the one or more processors are further caused to perform operations comprising providing information related to the blood coagulation characteristic, based at least in part on the accumulative property.

5. The device as recited in claim 4, further comprising a display, the providing information related to the blood coagulation characteristic further comprising presenting the information related to the blood coagulation characteristic on the display.

6. The device as recited in claim 4, further comprising a communication interface, the providing the information related to the blood coagulation characteristic further comprising sending the information related to the blood coagulation characteristic to a computing device.

7. The device as recited in claim 4, the providing the information related to the blood coagulation characteristic further comprising storing the information related to the blood coagulation characteristic on the computer-readable media.

8. A system comprising:
a sample receiver to receive a blood sample, the sample receiver comprising a plurality of electrodes arranged such that the plurality of electrodes and at least part of the blood sample are connected in a circuit;
one or more processors; and
computer-readable media storing executable instructions, which when executed, cause the one or more processors to perform operations comprising:
causing an electrical potential difference to be applied across the at least part of the blood sample;
receiving, over time, measurements of an electrical signal passing through the blood sample to obtain a plurality of measurements;
generating a measurement function of time from the plurality of measurements representing a change in a value of the electrical signal over time, the measurement function of time having a first peak, a first bottom, and a second peak; and
determining a blood coagulation characteristic based at least in part on the measurement function of time, wherein:
(a) the blood coagulation characteristic is Prothrombin Time (PT) and a PT value is determined at least in part by a ratio of (i) an area under the measurement function of time, above a zero value of the electrical signal, and between the first peak and the second peak and (ii) an area under the measurement function of time, above a value of the electrical signal at the first bottom, and between the first peak and the second peak;
(b) the blood coagulation characteristic is Activated Partial Thromboplastin Time (APTT) or Thrombin Time (TT) and an APTT value or TT value is determined at least in part by a summation of (i) an area between the first peak and the first bottom that is above the measurement function of time and below a value of the electrical signal at the first peak and (ii) an area between the first bottom and the second peak that is above the measurement function of time and below a value of the electrical signal at the second peak; or
(c) the blood coagulation characteristic is fibrinogen content (FIB) and a FIB value is determined at least in part by a difference between a value of the electrical signal at the first peak and a value of the electrical signal at the first bottom.

9. The system as recited in claim 8, wherein the determining the blood coagulation characteristic further comprises sending the measurement function of time to a computing device.

10. The system as recited in claim 8, further comprising a display for displaying information related to the blood coagulation characteristic.

11. A device comprising:
a sample receiver to receive a blood sample, the sample receiver comprising a plurality of electrodes arranged such that the plurality of electrodes and at least part of the blood sample are connected in a circuit; and
one or more processors connected to the sample receiver and configured to perform operations comprising:
causing an electrical signal to be applied across the blood sample;
receiving measurements of the electrical signal over a time duration to obtain a plurality of measurements;
generating a measurement function of time representing the plurality of measurements plotted against time, the measurement function having a first peak, a first bottom, and a second peak; and
determining a blood coagulation characteristic of the blood sample based at least on the measurement function of time, wherein:
(a) the blood coagulation characteristic is Prothrombin Time (PT) and a PT value is determined at least in part by a ratio of (i) an area under the measurement function of time, above a zero value of the electrical signal, and between the first peak and the second peak and (ii) an area under the measurement function of time, above a value of the electrical signal at the first bottom, and between the first peak and the second peak;
(b) the blood coagulation characteristic is Activated Partial Thromboplastin Time (APTT) or Thrombin Time (TT) and an APTT value or TT value is determined at least in part by a summation of (i) an area between the first peak and the first bottom that is above the measurement function of time and below a value of the electrical signal at the first peak and (ii) an area between the first bottom and the second peak that is above the measurement function of time and below a value of the electrical signal at the second peak; or
(c) the blood coagulation characteristic is fibrinogen content (FIB) and a FIB value is determined at least in part by a difference between a value of the electrical signal at the first peak and a value of the electrical signal at the first bottom.

12. The device as recited in claim 11, further comprising a sample receptor for receiving the blood sample, wherein the sample receptor includes at least one of:
a reagent for PT measurement, and the blood coagulation characteristic is correlated to PT; or
a reagent for APTT measurement, and the blood coagulation characteristic is correlated to APTT.

13. The device as recited in claim 11, wherein the blood coagulation characteristic is a function of an amplitude difference between the first peak and the first bottom of the measurement function of time.

14. The device as recited in claim 11, wherein the blood sample is prepared for measuring FIB, and the blood coagulation characteristic is correlated to FIB.

15. The device as recited in claim 11, wherein the electrical signal is current measured between at least two of the plurality of electrodes.

16. The device as recited in claim 11, wherein the electrical signal is voltage measured between at least two of the plurality of electrodes.

* * * * *